United States Patent [19]

Seuss, deceased et al.

[11] 4,364,378
[45] Dec. 21, 1982

[54] MASSAGE APPARATUS WITH ELECTROSTATIC FIELD

[76] Inventors: Willy Seuss, deceased, late of Müchen, Fed. Rep. of Germany; by Fride Seuss née Falter, executrix, Rembrandtstr, 5, 8000 Müchen, Fed. Rep. of Germany

[21] Appl. No.: 159,838

[22] Filed: Jun. 16, 1980

Related U.S. Application Data

[63] Continuation-in-part of Ser. No. 844,186, Oct. 21, 1977, abandoned.

[30] Foreign Application Priority Data

Oct. 22, 1976 [DE] Fed. Rep. of Germany ....... 2647947

[51] Int. Cl.³ ............................................. A61H 21/00
[52] U.S. Cl. ..................................... 128/24.5; 128/49
[58] Field of Search ...................... 128/242, 41, 48, 49, 128/51, 52, 24.2, 32, 36, 24.1, 783; D24/40; 164/0.55

[56] References Cited

U.S. PATENT DOCUMENTS

| | | | |
|---|---|---|---|
| 1,262,669 | 4/1918 | Hircta | 128/24.1 |
| 1,559,743 | 11/1925 | Geissler | 128/24.1 |
| 1,680,086 | 8/1928 | Carlson | 128/24.1 |
| 1,955,863 | 4/1934 | Schmidt | 128/24.1 |
| 2,021,968 | 11/1935 | Scherdegger | 128/24.1 |
| 2,022,457 | 11/1935 | Brown | 128/24.1 |
| 3,096,758 | 7/1963 | Savage | 128/41 |
| 3,710,785 | 1/1973 | Hilger | 128/24.2 |
| 3,750,672 | 8/1973 | Berckheim | 128/376 |
| 3,848,588 | 11/1974 | Miquel | 128/41 |

FOREIGN PATENT DOCUMENTS

| | | | |
|---|---|---|---|
| 285415 | 6/1964 | Australia | 128/783 |
| 1053584 | 4/1952 | France | 128/24.1 |
| 600896 | 12/1977 | Switzerland | 128/783 |
| 11844 | of 1886 | United Kingdom | 128/783 |
| 469471 | 8/1975 | U.S.S.R. | 128/404 |

Primary Examiner—Richard C. Pinkham
Assistant Examiner—T. Brown
Attorney, Agent, or Firm—Toren, McGeady and Stanger

[57] ABSTRACT

A massage apparatus is described which comprises an electrical switching circuit, a first massaging unit comprising an electromagnetic oscillator and bearing a vibrator head of electrically conductive material bearing an insulating coating. Electrical lines connect the posts of a first plus pole and of a first minus pole in the electric switching circuit with the electromagnetic oscillator and another electric line connects one of the posts of a second plus pole or a second minus pole in the circuit with the vibrator head serving as a first electrode, and laying-on electrode or another vibrator head are connected to the other post of the said second plus pole or second minus pole, thus establishing an electrostatic field between the two electrodes, through the body of the person to be treated, acting as the dielectric.

6 Claims, 7 Drawing Figures

MASSAGE APPARATUS WITH ELECTROSTATIC FIELD

RELATIONSHIP TO EARLIER APPLICATION

This application is a continuation-in-part of my pending patent application Ser. No. 844,186 (abandoned) filed Oct. 21, 1977.

BACKGROUND OF THE INVENTION

This invention relates to an apparatus comprising a periodically movable unit for massaging the skin of a person being treated and driving means for setting this unit in motion.

I have occupied myself for years with bioelectric processes and their therapeutical evaluation. Thus, I have recognized the medical possibilities of a magnetic field about 20 years ago and was one of the first to offer concrete evidence of its effects which was confirmed by the University of München, Germany in a detailed scientific work.

Furthermore, I have occupied myself with electric fields and their therapeutical applicability. Thus, in my German Pat. No. 1,177,282, laid open on Sept. 3, 1964, I disclosed the application of a dressing for the treatment of wounds, which dressing bears on a face thereof provided with an adhesive, a flexible capacitor, preferably consisting of two metal layers, e.g. silver foil applied on both sides of a strip of paper serving as dielectric layer, in order to achieve relaxation of tension and inhibition of inflammation, e.g. of the joints such as periarthritis, epicondylitis and also in the treatment of digenerative arthrosis.

In my German Pat. No. 1,171,095, laid open on May 27, 1964, I described the beneficial cumulative effects of heat, for instance applied in the form of a heating pad, and of an electric direct voltage field or a low-frequency alternating field which field is applied to the heated body portion by means of electrodes which are insulated against the body of the person to be treated.

In this case at least two heating pads should be applied on both sides of a body portion to be treated, and direct current, pulsating direct current or alternating current from the publics electric mains can be applied to the heating pads with opposite polarity to produce an electric field between them. Also, when alternating current is fed to the heating pads, at least one of the latter is provided with an additional lead connected to a direct voltage potential, thus enabling formation of a well-defined electrostatic field, preferably, this lead is connected to a rectifier fed with alternating voltage from the mains.

The main work of the inventor as a physician was in chirotherapy in which a special kind of massage is often carried out. On the basis of his knowledge in the field of electrotherapy, especially of treatment with electric fields, he conceived the usefulness of combining manual therapy with electrotherapeutical measures and it is the object of the instant invention to find a combination of both.

A variety of different massage apparatus are in the market. The most common type of these apparatus is a vibrator-type massage apparatus which runs on alternating current and in which the electric vibrations are transformed into mechanical vibrations by means of a coil and an armature and are then transmitted to the vibrator head. The vibrator head is placed on the body of the person to be treated and transmits its vertical vibrations to it.

An evident drawback of the mechanical massage compared with the manual massage resided up to now in the fact that it could not be adequately adapted to the anatomical facts and the different indications of the person being treated.

Thus, for instance, the mechanical massage of persons of different age or different height or corpulence is presently carried out with the same frequency and intensity. In order to achieve the same in-depth effect in the case of corpulent persons, a larger force is needed than with slim persons, slim persons often experience even a normal massage as unpleasant. Even more important is the adaptation to the different types of diseases, status of sickness and types of tissues.

OBJECT AND SUMMARY OF THE INVENTION

It is, therefore, a first object of the present invention to attain the above-described combination therapy of a "massage in an electrostatic field" by purely mechanical means, i.e. without the necessity of a massage with the hand, while offering all possibilities of a hand massage, namely, adjusting the intensity of the massage to the local physical conditions of the treated person, and, at the choice of the operator, with very strong intensity on bony parts, with strong intensity on sinews and tendons, with a medium intensity on muscles and with an intensity being as weak as possible on nerves and when treating organs by penetrating vibrations produced on the superimposed skin portions.

It is another object of my invention to provide for improvements in conventional massage apparatus and a circuitry devised for the control of such massage apparatus, whereby the manifold requirements of massage described hereinbefore can be satisfactorily met, in conjunction with the application of an electrostatic field.

Thus, the above-described objects are attained, according to the invention, in a massage apparatus for massaging the skin of a person to be treated which apparatus comprises (a) an electric switching circuit adapted to be connected to a source of alternating electric current and comprising a rectifying unit and a current supply means for generating a first, periodically interrupted D.C. voltage between a first plus pole and a first minus pole, linear voltage regulator means for generating a second D.C. voltage between a second plus pole and a second minus pole, and comprising posts for the connection of lines for each of said poles and frequency control means adapted for infinitely varying the periodic interruptions of said first D.C. voltage, applied to said first minus pole and said first plus pole, in the range of from 5 to 50 cycles, (b) a first massaging unit comprising a housing, electromagnetic oscillator means adapted for producing mechanical oscillation and comprising electromagnetic coil means and armature means, said armature means having a free oscillatable armature end, and a vibrator head of electrically conductive material and having a flat part and an electrically insulating coating covering said flat part, said vibrator head being destined to be placed with the electrically insulating coating of said flat part on a first region of the skin of a person to be treated, and said vibrator head having an electrically conductive neck portion, facing away from said flat part and being mounted on said free oscillatable armature end in such a position that at least said flat vibrator head part is outside said housing, and the oscillations of said vibrator head occur along an axis extending substantially vertically to the skin portion contacted by said first part, (c) coil-energizing current supply circuit comprising second rectifier means for producing a D.C. supply voltage and having output posts, the electromagnetic coil means being connected across the said output posts, (d) electric lines connected to the posts of said first plus pole and to said first minus pole, on the one hand, and to said electromagnetic coil means on the other hand, whereby said electromagnetic coil means are energized interruptedly in harmony with said first, periodically interrupted D.C. voltage, (e) an electric line connected to one of the posts of said second plus pole and said second minus pole, on the one hand, and to said electrically conductive neck portion, to apply the respective pole of said second D.C. voltage to said flat part of said vibrator head, whereby said flat part constitutes a first electrode, (f) a second electrode unit of electrically conductive material and having a flat part adapted for being placed on a second region of the skin of the same person to be treated, on the opposite side of the body portion from where said vibrator head flat part defined under (b) is placed on the skin, that body portion constituting a dielectric layer between said first and second electrodes, (g) a separate electric line connected to the other one of the posts of said second plus pole and said second minus pole, on the other hand, and to said second electrode unit thereby establishing an electrostatic field of said second D.C. voltage, between said flat part of said vibrator head and said flat part of said second electrode unit, as capacitor plates, and through the body of the person to be treated, acting as the dielectric therebetween, and wherein said linear voltage regulator means for generating said second D.C. voltage comprise potentiometer means for adjusting the strength and polarity of said electrostatic field.

A decisive improvement of known methods of mechanical massage is achieved in the treatment with a massage apparatus according to the invention, by providing a continuous intensity regulation.

An important feature of the present invention resides in that the mechanical vibrations, which are e.g. produced by a vibrator, are continuously adjustable between a frequency of 5 to 50 cycles. Hereby, the mechanical massage can be better adjusted to the requirements of different types of tissue and/or disease.

Similar to the way in which the effect of a mechanical stimulus depends on its intensity, in electrotherapy, this effect depends on the amount of stimuli per time unit, i.e. the frequency. Due to my experience in this field, I have found mechanical vibrations in a frequency range of 5 to 20 cycles to be therapeutically most advantageous, except for the treatment of nerves.

The following rough rule can be followed: for the massage of bony parts 12 to 15 cycles, of sinews or tendons 15 to 18 cycles, of muscles about 20 cycles, of organs 10 cycles and of nerves 40 to 50 cycles.

Changes in the stated frequencies can become necessary for different reasons, e.g. specific individual conditions-these changes can be made by the treating physician.

It has been found that straight vibrations of 60 cycles as they are usual in electric massage apparatus running on alternating current are less needed and therefore less effective.

The method of continuous frequency regulation according to the invention thus achieves another decisive improvement of mechanical massage, because the frequency can be adapted to the special requirements of the treated person.

Another important feature of the invention resides in the use of direct current fields. I have found in my practice that direct current fields achieve a specially strong analgesic and relaxing effect. These effects were confirmed in several scientific studies. The analgesic effect of a direct current field is strongest when the electrode of the vibrator head is connected with the minus-pole of the current source. Thereby, a softening of hardened tissue and a secondary infection-inhibiting and blood circulation-promoting effect via the vegetative nerve system is achieved.

Analgesia and relaxation also occur when the electrode of the vibrator head is connected with the plus pole of the current source; however the effect is somewhat smaller. On the other hand, a stronger tonic effect can usually be registered in this case, especially on the muscular system, but also on the tissues and nerves.

A "laying-on electrode" is an electrode destined to be laid on, or attached to, the skin of a person to be treated.

BRIEF DESCRIPTION OF THE DRAWINGS

Preferred embodiments of the massage apparatus according to the invention will now be described in greater detail by reference to the accompanying drawings, in which.

DETAILED DESCRIPTION OF THE EMBODIMENTS SHOWN IN THE DRAWINGS

Figure 1:
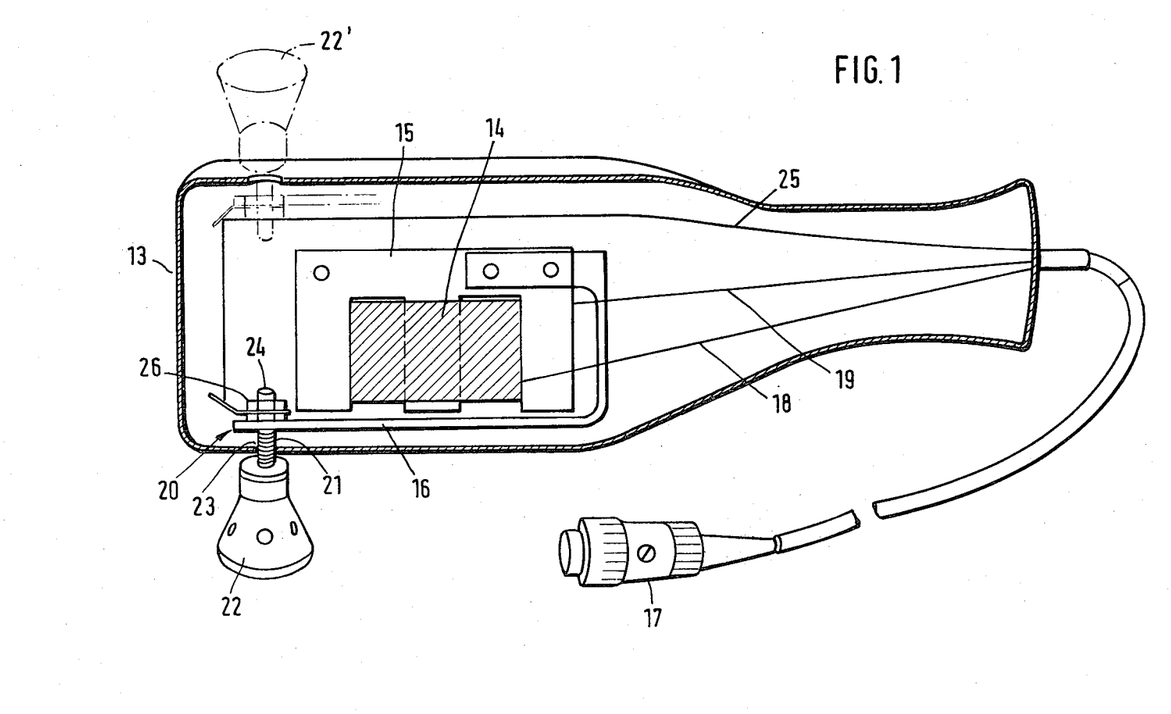
FIG. 1 shows schematically and partly in perspective a massage apparatus according to the invention bearing a preferred embodiment of a vibrator head.

FIG. 1 shows a massage apparatus adapted for producing electrostatic fields. The apparatus comprises a housing 13 of elongated bottle shape, in which there is mounted an electromagnetic coil 14, a stationary magnetic core 15, and an oscillating armature 16 which is attracted or repelled when the electromagnetic coil is energized from an electrical current source (not shown) via a plug 17 and lead wires 18 and 19. At the free end 20 of the armature, serving as a supporting arm, there is mounted the shaft 21 being the neck portion of a vibrator head 22. The distance by which the vibrator head 22 is held to protrude from the housing 13, can be adjusted by means of a fastening nut 26 provided on a threaded end portion 24 of shaft 21. The vibrator head 22 represents an electrode according to the invention and is insulated against the armature 16. The shaft 21 of vibrator head 22 protrudes outside the housing 13 through a window 23 in the lateral wall thereof. At its end portion 24 projecting inwardly from the armature 16, shaft 21 can be connected via an electric lead 25 and plug 17 to the current source, to apply an electric field to vibrator head 22. The massage apparatus according to the invention can comprise one or two electrodes of this type each, on a vibrator head.

Bipolar fields can be produced e.g. by using two massage apparatus, wherein the polarities of the flat vibrator head parts of both apparatus must be opposite ones. But the electrostatic field can also be produced between a vibrator head as the first electrode and a usual hand-held or layed-on electrode, as the second electrode.

Figure 2:
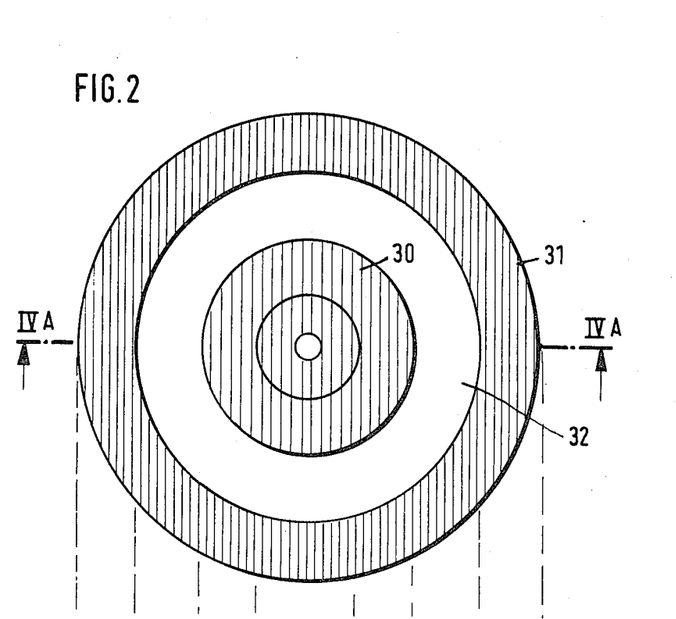
FIG. 2 is a plan view of another embodiment of a vibrator head connected with an annular electrode.
Figure 2A:
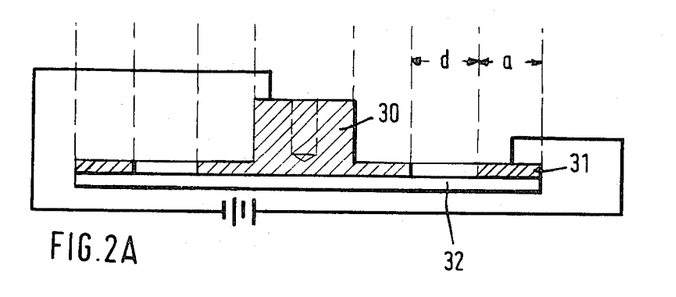
FIG. 2A shows the embodiment of FIG. 2 in a cross-sectional view taken along the plane II-IIA in FIG. 2.

FIG. 2 shows a so-called "ring electrode" serving as a second electrode for the generation of a bipolar field as described above. In this embodiment, there is provided around the vibrator head 30 another metal ring 31 having a width a of 1 centimeter and a distance d of 4 cm from the periphery of the vibrator head 30. The ring 31 is mechanically connected with the vibrator head 30 by means of a supporting disk 32 of electrically non-conducting plastics material and is thus only subjected to the same mechanical vibrations as vibrator head 30. In order to produce a bipolar field, this metal ring 31 is connected via a lead as shown in FIG. 2A with the plus pole and the vibrator head 30 is connected via another lead (not shown) with the minus pole of a source of electric current (not shown).

The first electrode is a plate or disk of metal and is preferably glued or screwed onto the base plate and is covered, and thereby electrically insulated from the skin of the treated body, by a synthetic plastics foil. The counter electrode can be a metallic base plate. Preferably, as in the apparatus of FIG. 2, the vibrator head serves by itself as the first electrode. The two electrodes can be screwed or glued on individual supports or, as in the embodiment of FIG. 2, on a common support. Of course, each electrode must be insulated from the other and from the remaining apparatus, e.g. by a coating of lacquer applied on the contact face of the electrode with the skin, and where the electrode comes into contact with the remainder of the electromagnetic unit.

As mentioned hereinbefore, adoption of the massage treatment with an apparatus according to my invention permits adjustment to a determined frequency range indicated by the state of health and the respective parts of the body of the person being treated. Moreover, the intensity and direction of the electric field about the massaging unit can be varied. This is achieved by means of a switching circuit as illustrated schematically in FIG. 3 and more in detail in FIGS. 4 to 7. It comprises, besides a plug or plugs for one or several massage apparatus, respectively, a transformer and an A.C. to D.C. rectifier as well as control devices for adjusting or setting the direct current voltage, the intensity of the massage vibrations and the frequency of the mechanical oscillations. Preferred is a direct current voltage of 9 to 40 volts and a frequency of the mechanical vibrations of 5 to 50 cycles.

The invention is further illustrated by a number of examples of how the same is carried out in practice.

EXAMPLE 1

Vibrator-massage apparatus with electric field via the head electrode with an additional electrode on the opposite side of the head.

Treatment of an acute case of crooked neck along the border of the trapezius muscle and paravertebral column with a massage apparatus equipped with a vibrator head and application of an electrostatic field. Already after 4 minutes the neck could be turned to the middle and even further. After two further treatments the mobility of the skeleton of the neck was restored and the patient out of pain.

EXAMPLE 2

A massage apparatus comprising a vibrator head and equipped with a ring electrode as shown in FIG. 2 and described supra, is used. The massage head is connected with the minus pole and the ring electrode with the plus pole of a D.C. source.

Treatment of a chronic cervical syndrom, mainly in the region of both shoulders, and the deltoid muscle, thereafter with a weaker vibrator adjustment directly above the skeleton of the neck. After six treatments a head-nape-ailment, persisting over years, and strains in the region of shoulder and occiput were completely eliminated.

EXAMPLE 3

Two massage apparatus with vibrator heads were connected to opposite electric poles, or a massage apparatus and a laid-on electrode were used.

Treatment of a stubborn ailment in the region of the lumbar vertebra and the sacrum, especially in the lumbosacral transition zone. The massage apparatus connected to the plus pole was applied on the right-hand side above the crest of the pelvis and the musculus glutaeus, and the apparatus connected to the minus pole was applied in the same region on the left-hand side; subsequently, treatment was continued with a massage apparatus connected to a D.C. plus pole and an electrode connected to the D.C. negative pole in contact with a hand of the treated person. After ten massages the state of the patient has substantially improved, above all no more pain is felt in a sitting position.

Figure 3:
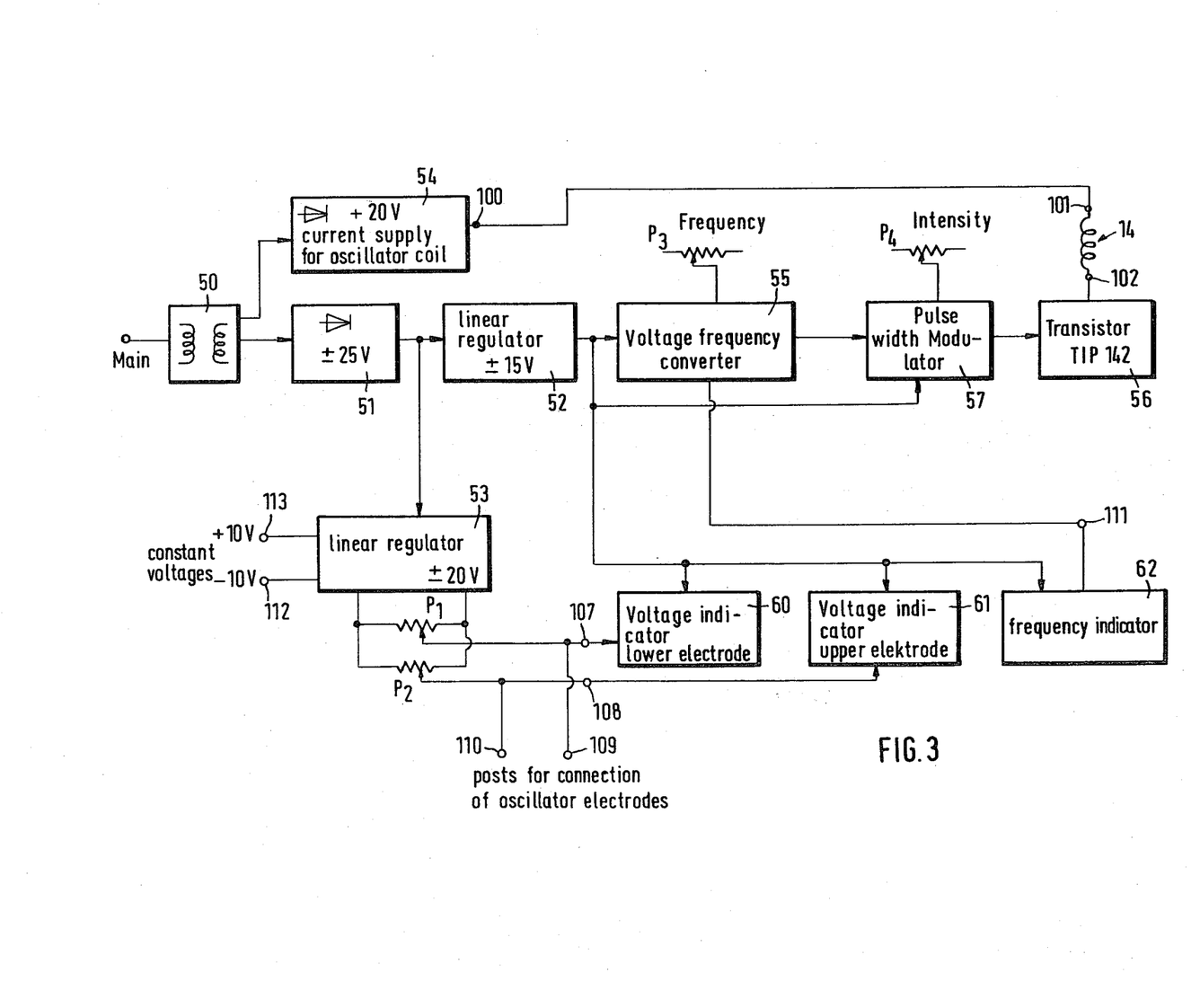
FIG. 3 shows a block diagram of an electric circuit to be connected to a vibrator head as shown in FIG. 2.

The block circuit illustrated in FIG. 3 comprises the following component blocks:

(a) a transformer 50 connected to the main; a dual linear voltage regulator comprising a rectifier unit 51 delivering ±25 V linear voltage and connected to a first linear voltage regulator 52 delivering a direct voltage of ±15 V and a second linear voltage regulator 53 delivering a direct voltage of ±20 V;

(b) a current supply unit 54 delivering a ±20 V direct voltage at its exit 100 is also connected to the output side of transformer 50. Post 100 of unit 54 is connected to contact post 101 of an oscillator coil of a vibrator, e.g. electromagnetic coil 14 of the massage apparatus shown in FIG. 3. The other post 102 of oscillator coil 14 is connected to a transistor 56, preferably a Darlington transistor circuit of the type TIP 142 manufactured by Texas Instruments Inc., Dallas, Tex.

A voltage-frequency converter 55 is connected to the −15 V post 103 of linear voltage regulator 52. Its circuit which is closed with the latter via post 100 (+15 V), is shown in detail in the left half of FIG. 7. It comprises a potentiometer P$_3$ to control the frequency of the oscillations generated by oscillating coil 14 and thereby the frequency of the mechanical oscillations of the vibrator head 22 (FIG. 1).

Also connected to the −15 V exit post 103 of linear voltage regulator 52 and to the output side of the voltage-frequency converter 55 is a pulse-width modulator 57 (right hand half of FIG. 8) which is connected to transistor 56 and comprises a potentiometer P$_4$ for controlling the intensity of the oscillations generated by oscillating coil 14 and thereby the length of the stroke or amplitude of mechanical oscillations of vibrator head 22.

Figure 4:
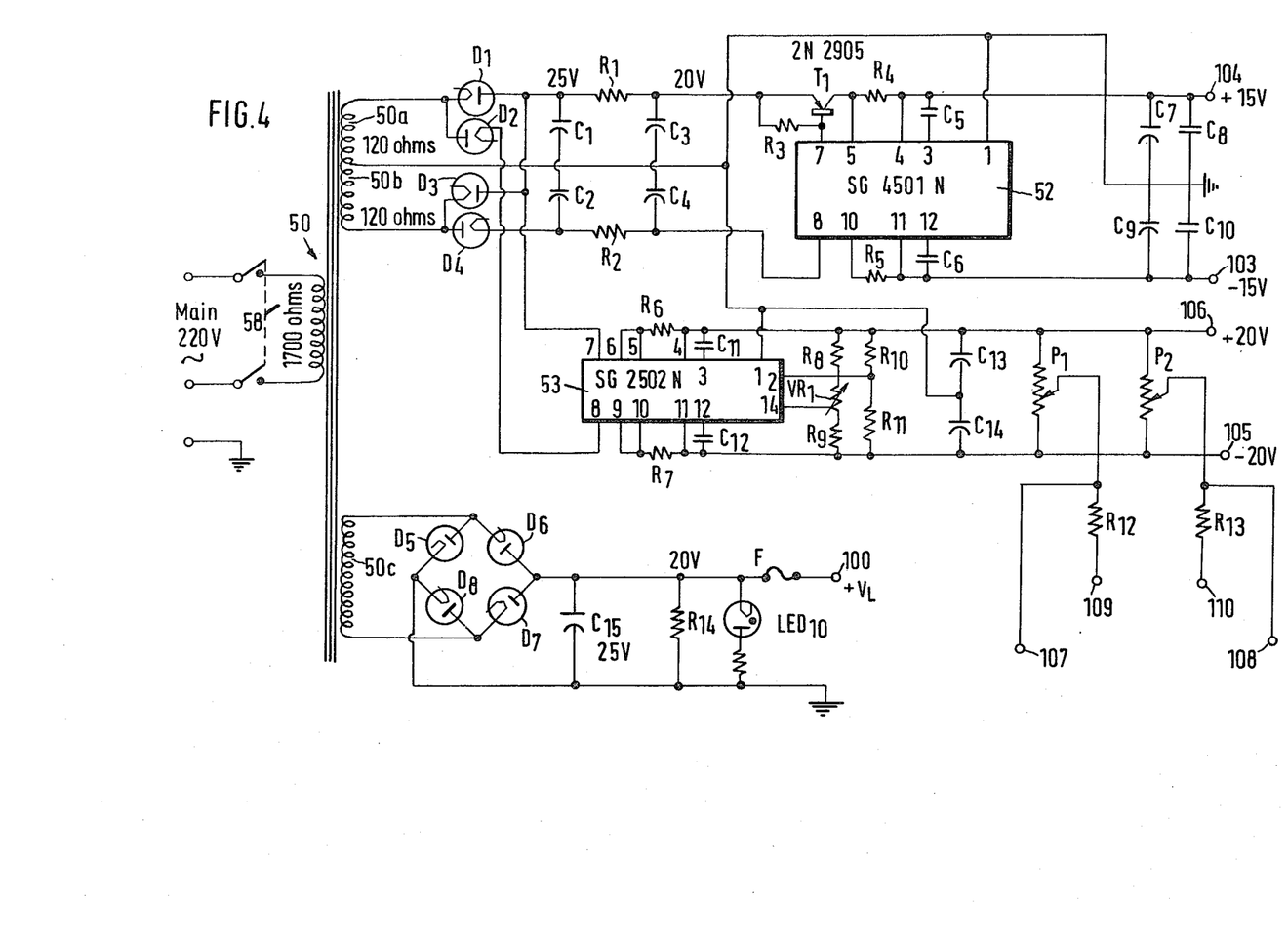
FIGS. 4, 5, 6 and 7 show separate portions of the electric circuit of FIG. 3, in more detail, as a preferred embodiment of the latter circuit.

The portion of FIG. 4 illustrating voltage regulator 53 is also shown in greater detail than in FIG. 3. Voltage regulator 53 comprises two potentiometers $P_1$ and $P_2$ of which potentiometer $P_1$ is connected via a first exit post 107 from second linear voltage regulator 53 to a first voltage indicator 60 for a first electrode, e.g. an electrode mounted on (lower) vibrator head 22 (FIG. 1), while the second potentiometer $P_2$ of linear regulator 53 is connected via a second exit post 108 from second linear voltage regulator 53 to a second voltage indicator 61 for a second electrode. Each of voltage indicators 60 and 61 comprises a light-emitting diode circuit to be described in detail hereinafter in connection with FIG. 5.

One of the contact posts 109 and 110 serves for the connection of the electrode of the vibrator head 22 to the switching circuit. The other one of the two posts is connected to the counter electrode. Contact posts 112 and 113 are connected to the front plate of the casing 13 of the massage apparatus and deliver a regulated voltage of ±10 V.

Voltage frequency converter 55 is connected via a post 111 to a frequency indicator 62 comprising a light-emitting diode circuit. This indicator 62 permits to read the frequency at which the oscillating coil 14 is energized, and accordingly the frequency of the mechanical vibrations of the vibrator head 22 of 22' respectively.

FIG. 4 shows a preferred embodiment of the circuit portion in the left half of FIG. 3.

The primary winding of the transformer 50 is laid out for 1700 ohms and is connected via a double pole switch 58 to the main supplying an A.C. of 220 V. Secondary windings 50a and 50b are each laid out for 180 ohms and are connected via four diodes $D_1$, $D_2$, $D_3$ and $D_4$ of Type IN4004, and other electrical members shown in FIG. 4 for delivery of a D.C. of −20 V to the dual linear voltage regulator 52 of the Type SG 4501 N, manufactured by Silicon General Inc., Westminster, Calif.

The posts of this voltage regulator 52 are numbered as shown in FIG. 4. This first voltage generator delivers D.C. of −15 V to an exit post 103 and of +15 V to an exit post 104. Secondary winding 50c of transformer 50 is also laid out for 180 ohms.

The circuit of voltage regulator 52 further comprises capacitors $C_1$ to $C_{10}$, resistors $R_1$ to $R_5$ and a transistor $T_1$ of the Type 2N Z905.

The same secondary windings 50a and 50b are also connected via rectifier diodes $D_1$, $D_2$, $D_3$ and $D_4$ of rectifier 51 to deliver a D.C. of 25 V to linear voltage regulator 53 of the Type SG 2502 N, also manufactured by Silicon General Inc. Dual voltage regulator 53 delivers, via the electrical members shown in FIG. 3, a D.C. voltage of −20 V to exit post 105 and of +20 V to exit post 106. The circuit of dual linear voltage regulator 53 further comprises resistors $R_6$ to $R_{11}$, capacitors $C_{11}$ to $C_{14}$ and a variable resistor $VR_1$.

Across the lines from voltage regulator 53 to posts 105 and 106 there are connected a potentiometer $P_1$ (100 k-ohm), the variable contact of which is connected to exit post 107 and also, via a resistor $R_{12}$ of 10 k-ohm, to post 109, and a potentiometer $P_2$ (100 k-ohm) the sliding contact of which is connected to exit post 108 and also, via a resistor $R_{13}$ of 10 k-ohm, to post 110. As mentioned hereinbefore the electrode of a first vibrator can be connected via line 25 (FIG. 1) to post 109.

In FIG. 4 there is also shown the current supply unit 54 for the oscillating coil 14. Unit 54 delivers D.C. voltage of 20 V via the post 100, the D.C. voltage is produced from A.C. voltage supplied from secondary winding 50c of transformer 50 in a set of four rectifier diodes of Type IN4004, shown as $D_5$, $D_6$, $D_7$, $D_8$, which set is also connected to earth. This unit 54 comprises further resistors $R_{14}$ and $R_{15}$, a capacitor $C_{15}$, a light-emitting diode $LED_{10}$ and a fuse F.

Figure 5:
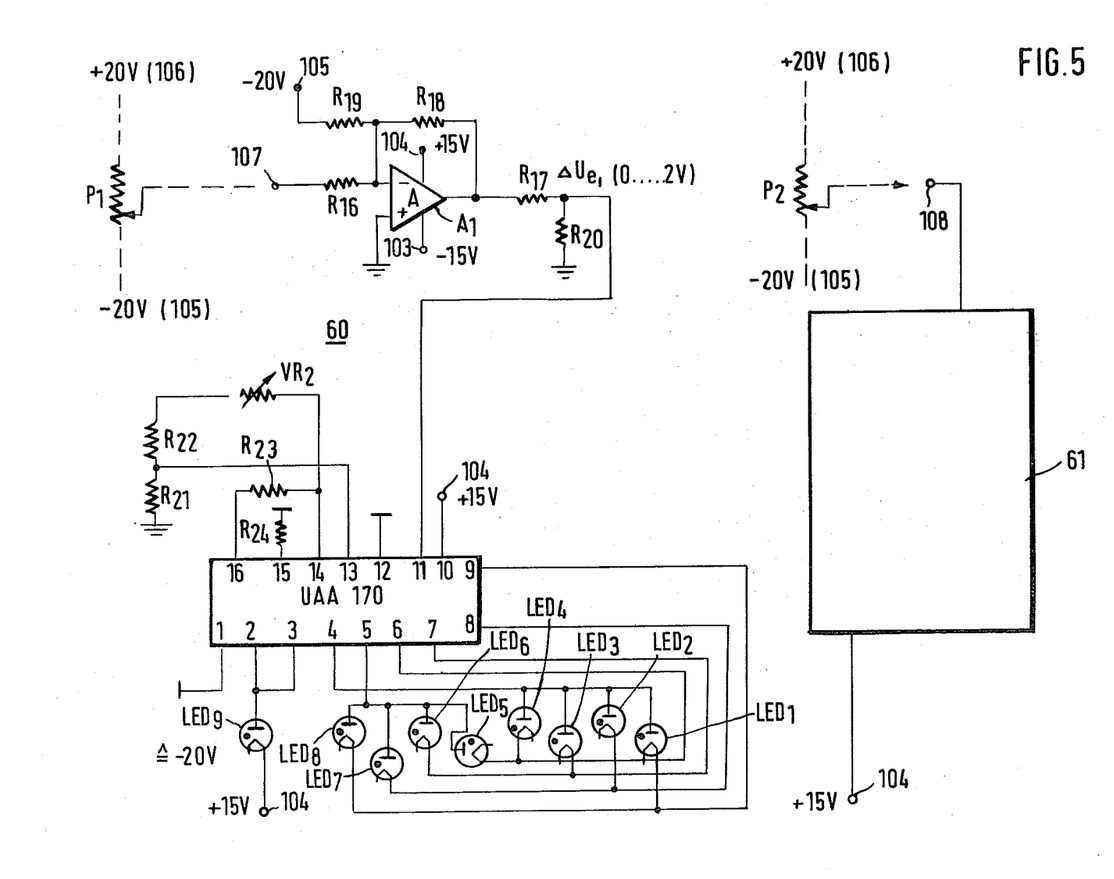

In FIG. 5 there is illustrated the indicating circuit 60 which is connected to exit post 107 of dual linear voltage regulator 53 as shown in FIG. 4, via the sliding contact of potentiometer $P_1$, which latter bridges the lines to posts 105 and 106. This indicating circuit 60 is connected with its other terminal to post 104.

The indicating circuit 61 is completely identical with indicating circuit 60, but is connected to post 108, on the one hand, and post 104 on the other hand. Post 108 is connected to the sliding contact of potentiometer $P_2$ in the manner shown in FIG. 4.

Indicating circuit 60 comprises an integrated circuit UAA 170 which has 16 pins and is manufactured by Siemens AG, München, Germany.

Pin 11 of this integrated circuit is connected to post 107 via a line which contains in series resistor $R_{16}$, amplifier $A_1$ and resistor $R_{17}$. Amplifier $A_1$ is connected to posts 103 and 104 and has a shunt resistor $R_{18}$ whose end connected to resistor $R_{16}$ is also connected via resistor $R_{19}$ to post 105. The line from resistor $R_{17}$ to pin 11 of integrated circuit UAA 170 is also connected to earth via a resistor $R_{20}$. Pins 1 and 12 of UAA 170 are grounded, pin 13 is grounded via a resistor $R_{21}$, pin 14 is grounded via the last-mentioned resistor $R_{21}$, but via interposed variable resistor $VR_2$ and resistor $R_{22}$. Pin 14 is also connected with pin 16 via shunt resistor $R_{23}$. Pin 15 is connected to earth via resistor $R_{24}$. Pins 4 to 9 are connected to eight light-emitting diodes $LED_1$ to $LED_8$ and pins 2 and 3 are connected to post 104 via a light-emitting diode $LED_9$.

Figure 6:
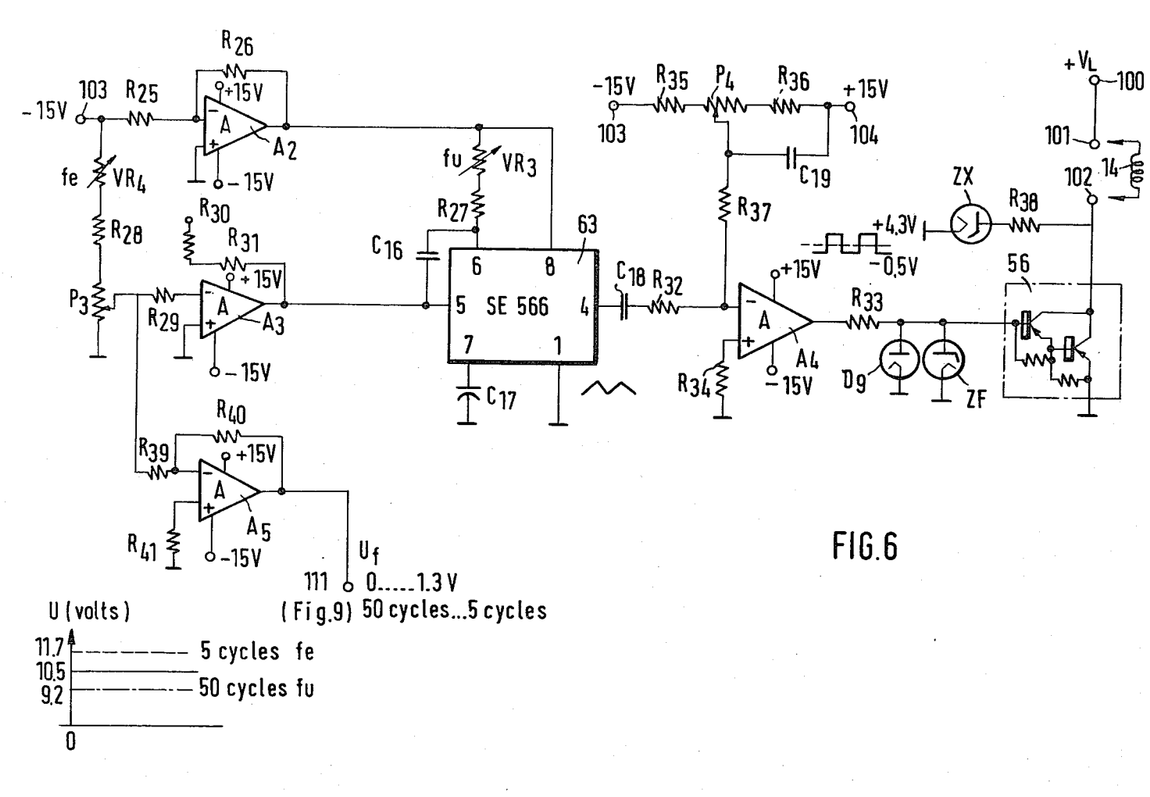

FIG. 6 shows in detail the circuit portions comprising the voltage frequency converter 55, the pulse width modulator 57 and the transistor 56 of FIG. 3.

The voltage frequency converter 55 comprises an integrated circuit 63 of Type SE 566 manufactured by Signatics International Corporation, London, England. Pins 5, 6 and 8 thereof are connected to exit post 103 of linear voltage regulator 52 (FIG. 4). Pin 8 of integrated circuit 63 is connected to post 103 via resistor $R_{25}$ and amplifier $A_2$ provided with a shunt resistor $R_{26}$; pin 6 of integrated circuit 63 (SE 566) is connected to the same amplifier $A_2$ via variable resistor $VR_3$ and resistor $R_{27}$; pin 5 of integrated circuit 63 is connected to post 103 via variable resistor $VR_4$, resistor $R_{28}$, potentiometer $P_3$, resistor $R_{29}$ and amplifier $A_3$ which latter is provided with a shunt circuit containing resistors $R_{30}$ and $R_{31}$. Pins 5 and 6 of integrated circuit 63 (SE 566) are connected with one another via a shunt capacitor $C_{16}$. Pin 7 of integrated circuit 63 is grounded via capacitor $C_{17}$. Variable resistor $VR_4$ determines the lower limit frequency $f_l$ (5 cycles), and the variable resistor $VR_3$ determines the upper limit frequency $f_u$ (50 cycles) of oscillator coil 14.

Amplifiers $A_1$, $A_2$ and $A_3$ as well as amplifiers $A_4$ and $A_5$, mentioned further below, preferably consist of two operational amplifiers of Type 747 in a single casing. Potentiometer $P_3$ serves to control the frequency of the oscillations of coil 14 as mentioned hereinbefore.

Integrated circuit 63 (SE 566) delivers via its exit pin 4 a sawtooth curve of voltage to the pulse width modulator 57 which comprises in a line from the exit pin 4 of SE 566 to the Darlington transistor 56, of Type TIP 142, in series, a capacitor $C_{18}$, a resistor $R_{32}$, an amplifier $A_4$ and a resistor $R_{33}$. The line from the latter to the entry post of transistor 56 is grounded first via a diode $D_9$ of Type 1N 4148 and, secondly, in parallel thereto, via a voltage limiting diode (Zener diode) ZF.

Amplifier $A_4$ acts as a comparator and produces a rectangular curve voltage. It is grounded via a resistor $R_{34}$.

Across posts 103 and 104, a connecting line contains in series a resistor $R_{35}$, the potentiometer $P_4$ for controlling the intensity of the oscillations of coil 14 and another resistor $R_{36}$. The sliding contact of potentiometer $P_4$ is connected via resistor $R_{37}$ to the line from resistor $R_{32}$ to amplifier $A_4$. A shunt capacitor $C_{19}$ is connected to post 104 and to the sliding contact of potentiometer $P_4$. The line from transistor 56 to post 102 of oscillator coil 14 is connected to earth via a resistor $R_{38}$ and, in series therewith, a Zener diode ZX, which acts as a transient suppressor diode.

The sliding contact of potentiometer $P_3$ is connected to exist post 111 (FIG. 3) by a line containing, in series, a resistor $R_{39}$ and an amplifier $A_5$, which is provided with a shunt resistor $R_{40}$ and is grounded via a resistor $R_{41}$.

In FIG. 9 there is shown in detail the frequency indicator 62 which comprises an integrated circuit UAA 170, of the same kind as mentioned hereinbefore (FIG. 5) the pin 11 of which is connected to post 111 (FIG. 6) via which post it received the voltage $U_f$.

Pins 1 and 12 to 16 of integrated circuit UAA 170 in frequency indicator 62 are connected to ground with the same circuitry as in FIG. 5, via a variable resistor $VR_5$ and resistors $R_{46}$, $R_{42}$, $R_{43}$ and $R_{44}$. Moreover, pins 11 and 12 are shunted via resistor $R_{45}$.

Pins 2 to 9 of integrated circuit UAA 170 in frequency indicator 62 are connected to sixteen light-emitting diodes $LED_{11}$ to $LED_{26}$.

Figure 7:
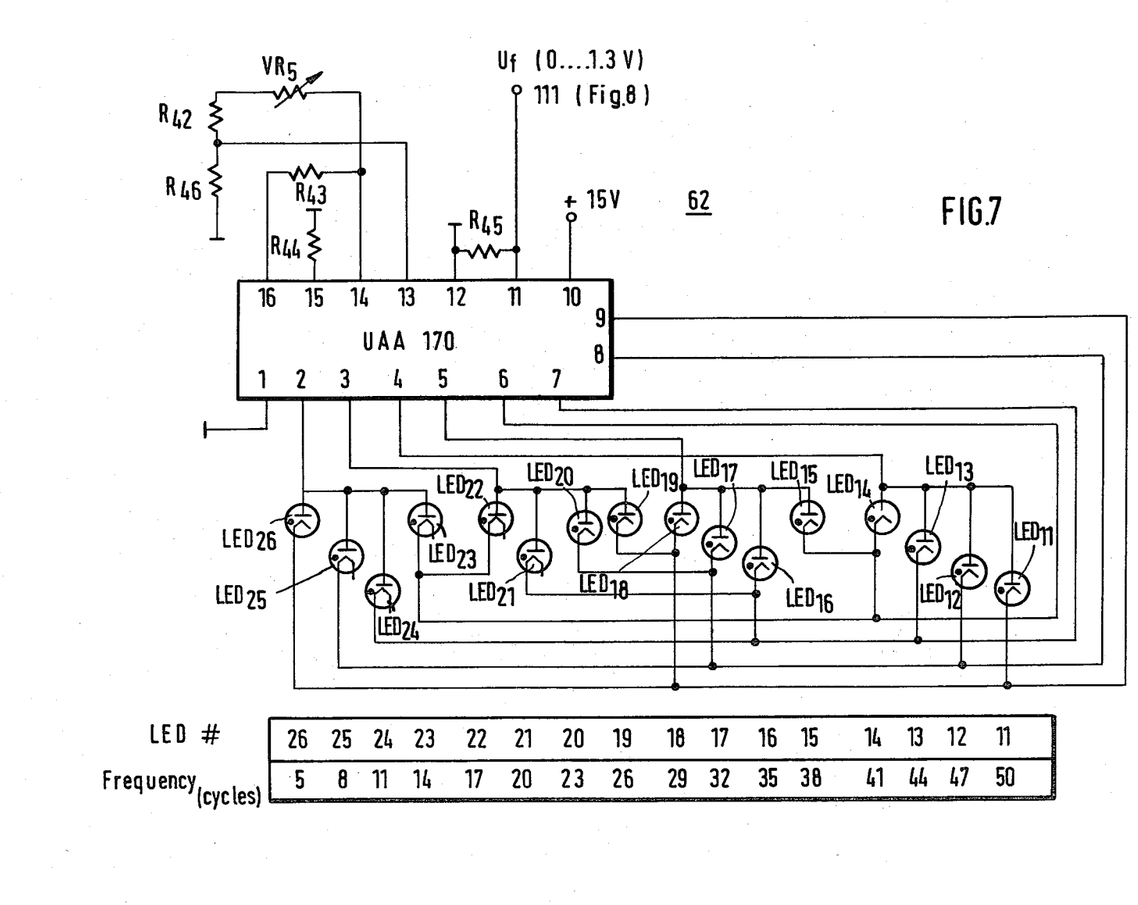

The frequency indicated by each of these diodes is seen in the box shown in FIG. 7 below the circuit.

The following table shows the data of each of the electrical members recommended in a best mode of building the oscillator control circuit shown in FIGS. 4 to 7. As diodes $D_1$ to $D_9$, there are recommended diodes of Type 1N 4004 manufactured by Siemens, AG, München, Germany. As a transformer I recommend Type MD 65 manufactured by Siemens AG, München, Germany.

As light-emitting diodes $LED_1$ to $LED_{26}$, I recommend Type TIL 220 manufactured by Texas Instruments Inc., Dallas, Tex.

| Fixed Resistors: | | | |
|---|---|---|---|
| $R_1$ | 39 ohms, 1 watt | $R_{24}$ | 1 k-ohm |
| $R_2$ | 150 ohms, 0.5 watt | $R_{25}$ | 30 k-ohms |
| $R_3$ | 100 ohms | $R_{26}$ | 24 k-ohms |
| $R_4$ | 2.7 ohms | $R_{27}$ | 12 k-ohms |
| $R_5$ | 10 ohms | $R_{28}$ | 15 k-ohms |
| $R_6$ | 10 ohms | $R_{29}$ | 1 megaohm |
| $R_7$ | 10 ohms | $R_{30}$ | 330 k-ohms |
| $R_8$ | 15 k-ohms | $R_{31}$ | 200 k-ohms |
| $R_9$ | 39 k-ohms | $R_{32}$ | 100 k-ohms |
| $R_{10}$ | 20 k-ohms | $R_{33}$ | 2.2 k-ohms |
| $R_{11}$ | 20 k-ohms | $R_{34}$ | 47 k-ohms |
| $R_{12}$ | 10 ohms | $R_{35}$ | 20 k-ohms |
| $R_{13}$ | 10 ohms | $R_{36}$ | 20 k-ohms |
| $R_{14}$ | 510 ohms, 1 watt | $R_{37}$ | 100 k-ohms |
| $R_{15}$ | 1 k-ohm | $R_{38}$ | 4.7 ohms |
| $R_{16}$ | 1 megaohm | $R_{39}$ | 1 megaohm |
| $R_{17}$ | 5.1 k-ohms | $R_{40}$ | 100 k-ohms |
| $R_{18}$ | 100 k-ohms | $R_{41}$ | 91 k-ohms |
| $R_{19}$ | 1 megaohm | $R_{42}$ | 5.6 k-ohms |
| $R_{20}$ | 5.1 k-ohms | $R_{43}$ | 20 k-ohms |
| $R_{21}$ | 7.5 k-ohms | $R_{44}$ | 1 k-ohm |
| $R_{22}$ | 2.4 k-ohms | $R_{45}$ | 10 k-ohms |
| $R_{23}$ | 20 k-ohms | $R_{46}$ | 2.2 k-ohms |
| Capacitors | | Variable Resistors | |
| $C_1$ | 470 microfarad, 40 volts | $VR_1$ | 5 k-ohms |
| $C_2$ | $= C_1$ | $VR_2$ | 1 k-ohm |
| $C_3$ | 10 microfarad, 35 volts | $VR_3$ | 2 k-ohms |
| $C_4$ | $= C_3$ | $VR_4$ | 10 k-ohms |
| $C_5$ | 33 nanofarad | | |
| $C_6$ | $= C_5$ | | |
| | | Potentiometers | |
| $C_7$ | microfarad, 20 volt | $P_1$ | 100 k-ohms |
| $C_8$ | 33 nanofarad | $P_2$ | 100 k-ohms |
| $C_9$ | $= C_7$ | $P_3$ | 100 k-ohms |
| $C_{10}$ | $= C_8$ | $P_4$ | 1 k-ohm |
| $C_{11}$ | 33 nanofarad | | |
| $C_{12}$ | $= C_{11}$ | | |
| | | Diodes | |
| $C_{13}$ | 1 nanofarad, 35 volts | ZF | 4.3 volts |
| $C_{14}$ | $= C_{13}$ | ZX | 68 volts |
| $C_{15}$ | 4700 microfarad, 25 volts | | |
| $C_{16}$ | 1 nanofarad | | |
| $C_{17}$ | 1 microfarad | | |
| $C_{18}$ | 1 microfarad | | |
| $C_{19}$ | 1 microfarad | | |

I claim:

1. A massage apparatus for massaging the skin of a person to be treated which apparatus comprises
   (a) an electrical switching circuit adapted to be connected to a source of alternating electric current and comprising a rectifying unit and a current supply means for generating a first, periodically interrupted D.C. voltage between a first plus pole and a first minus pole, linear voltage regulator means for generating a second D.C. voltage between a second plus pole and a second minus pole, and comprising posts for the connection of lines for each of said poles and frequency control means adapted for infinitely varying the periodic interruptions of said first D.C. voltage, applied to said first minus pole and said first plus pole, in the range of from 5 to 50 cycles,
   (b) a first massaging unit comprising a housing, electromagnetic oscillator means adapted for producing mechanical oscillation and comprising electromagnetic coil means and armature means, said armature means having a free oscillatable armature end, and
   a vibrator head of electrically conductive material and having a flat part and an electrically insulating coating covering said flat part, said vibrator head being destined to be placed with the electrically insulating coating of said flat part on a first region of the skin of a person to be treated, and said vibrator head having an electrically conductive neck portion, facing away from said flat part and being mounted on said free oscillatable armature end in such a position that at least said flat vibrator head part is outside said housing, and the oscillations of said vibrator head occur along an axis extending substantially vertically to the skin portion contacted by said flat part, (c) coil-energizing current supply circuit comprising said rectifier means for producing a D.C. supply voltage and having output posts, said electromagnetic coil means being connected across said output posts, (d) electric lines connected to the posts of said first plus pole and to said first minus pole, on the one hand, and to said current supply circuit on the other hand, whereby said electromagnetic coil means are energized interruptedly in harmony with said first, periodically interrupted D.C. voltage, (e) an electric line connected to one of the posts of said second plus pole and said second minus pole, on the one hand, and to said electrically conductive neck portion, to apply the respective pole of said second D.C. voltage to said flat part of said vibrator head, whereby said flat part constitutes a first electrode, (f) a second electrode unit of electrically conductive material and having a flat part adapted for being placed on a second region of the skin of the same person to be treated, on the opposite side of the body portion from where said vibrator head flat part defined under (b) is placed on the skin, that body portion constituting a dielectric layer between said first and second electrodes, (g) a separate electric line connected to the other one of the posts of said second plus pole and said second minus pole, on the one hand, and to said second electrode unit, thereby establishing an electrostatic field of said second D.C. voltage, between said flat part of said vibrator head and said flat part of said second electrode unit, as capacitor plates, and through the body of the person to be treated, acting as the dielectric therebetween, and wherein said linear voltage regulator means for generating said second D.C. voltage comprise potentiometer means for adjusting the strength and polarity of said electrostatic field.

2. The massage apparatus of claim 1, wherein said frequency control means are adapted for infinitely varying said periodic interruptions in the range of from 5 to 20 cycles, and wherein said electric line defined under (e) is connected to said second minus pole.

3. The massage apparatus of claim 1 or 2, wherein said second electrode unit is a separate vibrator head as defined under (b).

4. The massage apparatus of claim 1, wherein said current supply means are adapted for generating said first, periodically interrupted D.C. voltage as a square waveform.

5. The massage apparatus of claim 4, wherein said potentiometer means is adapted for infinitively varying said second D.C. voltage between the posts for said second plus pole and said second minus pole over the range of from 9 to 40 volts.

6. The massage apparatus of claim 1, wherein said current supply means for generating said periodically interrupted D.C. voltage further comprise pulse width modulator means comprising
an amplifier having a minus entry post and an outlet post, and
a potentiometer circuit being connected to the posts of said first minus pole and said first plus pole and having a slider, said slider being connected to said minus entry post,
said frequency control means having an outlet line for said periodically interrupted D.C. voltage in sawtooth form, which outlet line is connected to said minus entry post of said amplifier,
said coil-energizing current supply circuit further comprising Darlington transistor means, having a transistor base,
and an electric line connecting said outlet post of said amplifier with said transistor base and applying thereto rectangular D.C. voltage generated in said amplifier.

* * * * *